(12) United States Patent
Kim et al.

(10) Patent No.: US 9,232,932 B2
(45) Date of Patent: Jan. 12, 2016

(54) PROVIDING MOTION MODE IMAGE IN ULTRASOUND SYSTEM

(75) Inventors: Min Woo Kim, Seoul (KR); Woo Hyun Kang, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 7 days.

(21) Appl. No.: 13/620,619

(22) Filed: Sep. 14, 2012

(65) Prior Publication Data

US 2013/0165783 A1    Jun. 27, 2013

(30) Foreign Application Priority Data

Dec. 27, 2011  (KR) .................. 10-2011-0143854

(51) Int. Cl.
| | |
|---|---|
| A61B 8/00 | (2006.01) |
| A61B 8/06 | (2006.01) |
| G01S 15/89 | (2006.01) |
| G10K 11/34 | (2006.01) |
| A61B 8/08 | (2006.01) |
| G01S 7/52 | (2006.01) |

(52) U.S. Cl.
CPC . *A61B 8/06* (2013.01); *A61B 8/463* (2013.01); *A61B 8/469* (2013.01); *A61B 8/486* (2013.01); *A61B 8/488* (2013.01); *A61B 8/5246* (2013.01); *G01S 7/52085* (2013.01); *G01S 15/8984* (2013.01); *G10K 11/34* (2013.01); *A61B 8/0883* (2013.01); *A61B 8/0891* (2013.01); *A61B 8/4483* (2013.01); *A61B 8/5207* (2013.01); *G01S 7/52074* (2013.01)

(58) Field of Classification Search
CPC .................................. A61B 8/52; A61B 8/00
See application file for complete search history.

(56) References Cited

U.S. PATENT DOCUMENTS 6,023,977 A  *  2/2000  Langdon et al. ................. 73/629
2006/0122505 A1 *  6/2006  Dala-Krishna ............... 600/437

(Continued)

FOREIGN PATENT DOCUMENTS

EP        2264483 A2     12/2010
JP        05-146438 A     6/1993

(Continued)

OTHER PUBLICATIONS

Extended European Search Report issued in European Application No. 12184235.5 dated Apr. 23, 2013.
Pastorelli et al., "A Real-Time 2-D Vector Doppler System for Clinical Experimentation", IEEE Transactions on Medical Imaging, vol. 27, No. 10, Oct. 2008, pp. 1515-1524.

(Continued)

*Primary Examiner* — Mark Remaly
(74) *Attorney, Agent, or Firm* — McDermott Will & Emery LLP

(57) ABSTRACT

There are provided embodiments for providing a motion mode image corresponding to a motion of a target object. In one embodiment, by way of non-limiting example, an ultrasound system comprises: a user input unit configured to receive input information for setting a region of interest on a brightness mode image; and a processing unit configured to form the brightness mode image based on first ultrasound data corresponding to a target object and form vector information of the target object based on second ultrasound data corresponding to the target object, the processing unit being further configured to form a motion mode image including at least one of a brightness motion mode image and a color motion mode image based on the first ultrasound data and the vector information corresponding to the region of interest.

10 Claims, 17 Drawing Sheets

(56) References Cited

U.S. PATENT DOCUMENTS

2010/0256491 A1 10/2010 Lee et al.
2010/0305440 A1 12/2010 Lee et al.

FOREIGN PATENT DOCUMENTS

| JP | 07-075636 A | 3/1995 |
| JP | 08-000622 A | 1/1996 |
| JP | 2006-055493 A | 3/2006 |
| JP | 2009-050720 A | 3/2009 |
| KR | 10-2010-0111633 A | 10/2010 |
| KR | 10-2010-0129681 A | 12/2012 |

OTHER PUBLICATIONS

Pedersen et al., "Arterial secondary blood flow patterns visualized with vector flow ultrasound", 2011 IEEE Intl. Ultrasonics Symposium Proceedings, Oct. 18, 2011, pp. 1242-1245.
Korean Office Action issued in Korean Application No. 10-2011-0143854 dated May 15, 2013.
Korean Office Action issued in Korean Patent Application No. 10-2011-0143854 dated Nov. 28, 2013, with English translation, 6 pgs.
Notice of Allowance issued in Korean Patent Application No. 10-2011-0143854 dated Jan. 28, 2014, with English translation, 4 pgs.

\* cited by examiner

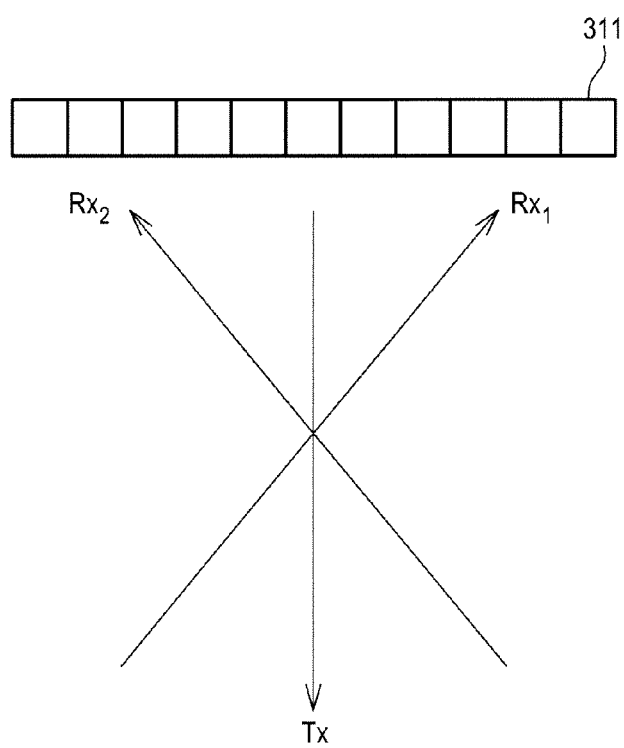

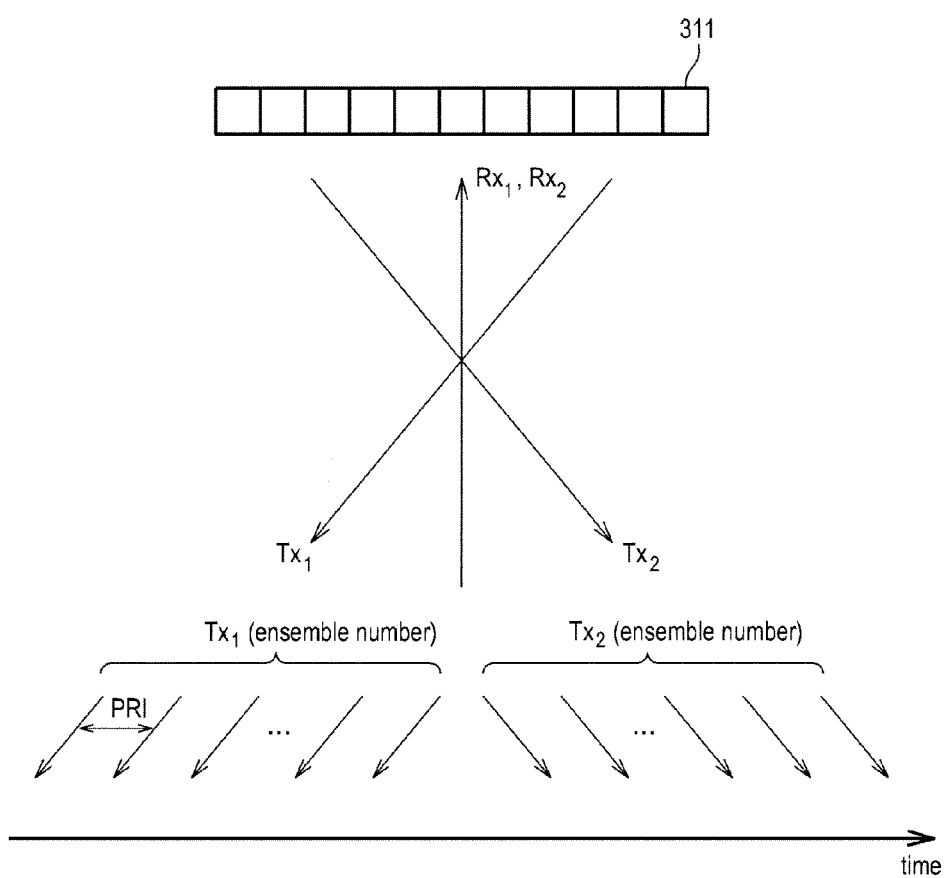

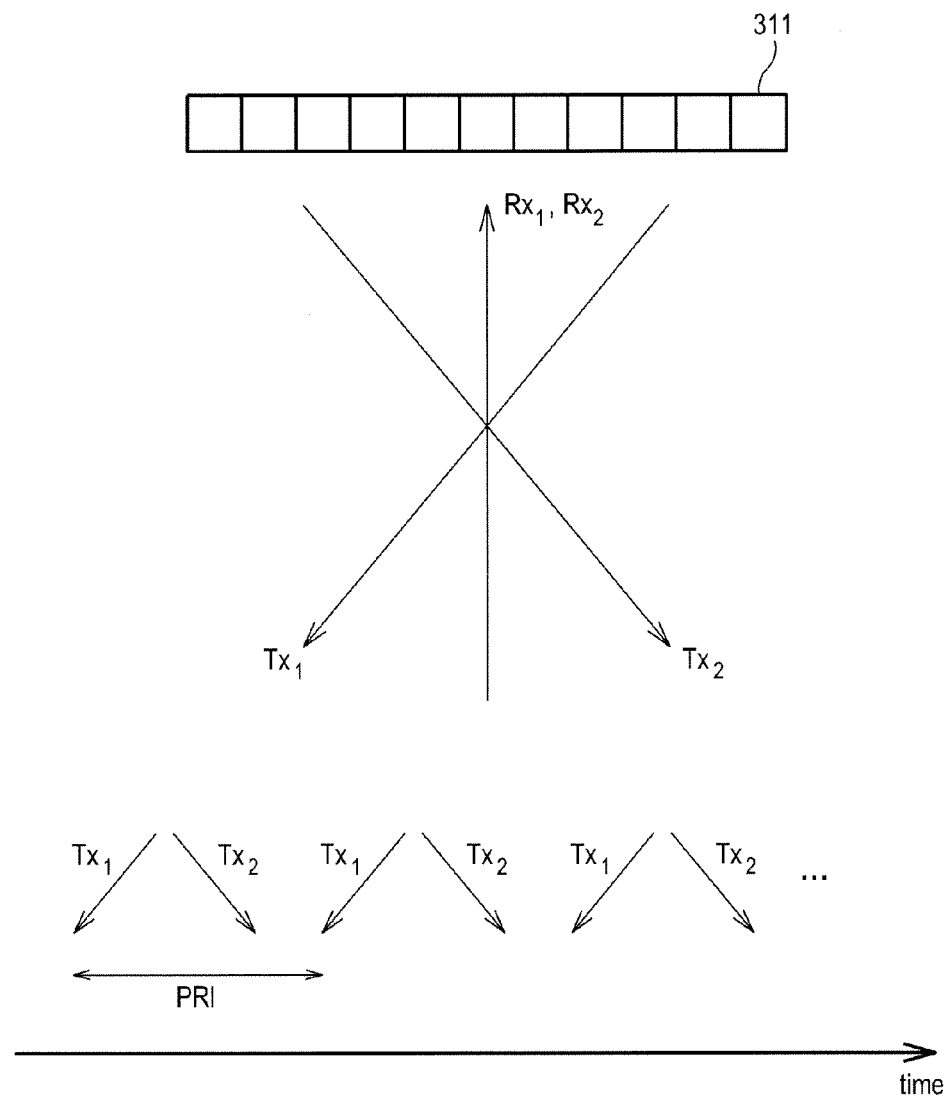

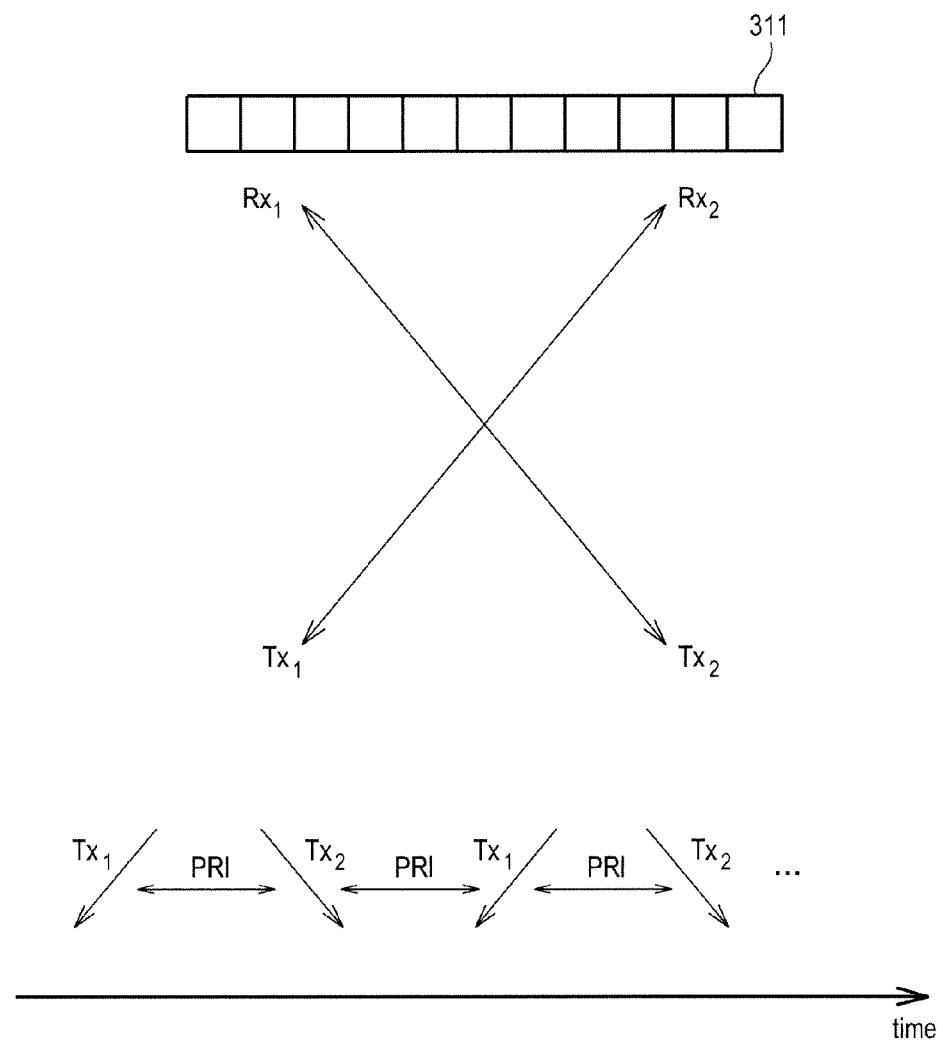

FIG. 8

| $S_{1,t}$ | $S_{2,t}$ | $S_{3,t}$ | $S_{4,t}$ | $S_{5,t}$ | $S_{6,t}$ | $S_{7,t}$ | $S_{8,t}$ | $S_{9,t}$ | $S_{10,t}$ | $S_{11,t}$ | ⋯ | $S_{p,t}$ |
|---|---|---|---|---|---|---|---|---|---|---|---|---|
| ⋮ | ⋮ | ⋮ | ⋮ | ⋮ | ⋮ | ⋮ | ⋮ | ⋮ | ⋮ | ⋮ | | ⋮ |
| $S_{1,6}$ | $S_{2,6}$ | $S_{3,6}$ | $S_{4,6}$ | $S_{5,6}$ | $S_{6,6}$ | $S_{7,6}$ | $S_{8,6}$ | $S_{9,6}$ | $S_{10,6}$ | $S_{11,6}$ | ⋯ | $S_{p,6}$ |
| $S_{1,5}$ | $S_{2,5}$ | $S_{3,5}$ | $S_{4,5}$ | $S_{5,5}$ | $S_{6,5}$ | $S_{7,5}$ | $S_{8,5}$ | $S_{9,5}$ | $S_{10,5}$ | $S_{11,5}$ | ⋯ | $S_{p,5}$ |
| $S_{1,4}$ | $S_{2,4}$ | $S_{3,4}$ | $S_{4,4}$ | $S_{5,4}$ | $S_{6,4}$ | $S_{7,4}$ | $S_{8,4}$ | $S_{9,4}$ | $S_{10,4}$ | $S_{11,4}$ | ⋯ | $S_{p,4}$ |
| $S_{1,3}$ | $S_{2,3}$ | $S_{3,3}$ | $S_{4,3}$ | $S_{5,3}$ | $S_{6,3}$ | $S_{7,3}$ | $S_{8,3}$ | $S_{9,3}$ | $S_{10,3}$ | $S_{11,3}$ | ⋯ | $S_{p,3}$ |
| $S_{1,2}$ | $S_{2,2}$ | $S_{3,2}$ | $S_{4,2}$ | $S_{5,2}$ | $S_{6,2}$ | $S_{7,2}$ | $S_{8,2}$ | $S_{9,2}$ | $S_{10,2}$ | $S_{11,2}$ | ⋯ | $S_{p,2}$ |
| $S_{1,1}$ | $S_{2,1}$ | $S_{3,1}$ | $S_{4,1}$ | $S_{5,1}$ | $S_{6,1}$ | $S_{7,1}$ | $S_{8,1}$ | $S_{9,1}$ | $S_{10,1}$ | $S_{11,1}$ | ⋯ | $S_{p,1}$ |
| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | ⋯ | $CH_p$ |

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | ⋯ | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | ⋯ | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | ⋯ | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | ⋯ | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | ⋯ | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | ⋯ | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | ⋯ | $P_{7,N}$ |
| ⋮ | ⋮ | ⋮ | ⋮ | ⋮ | ⋮ | ⋮ | ⋮ | ⋮ | | ⋮ |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | ⋯ | $P_{M,N}$ |

| $S_{1,t}$ | $S_{2,t}$ | $S_{3,t}$ | $S_{4,t}$ | $S_{5,t}$ | $S_{6,t}$ | $S_{7,t}$ | $S_{8,t}$ | $S_{9,t}$ | $S_{10,t}$ | $S_{11,t}$ | $\cdots$ | $S_{p,t}$ |
|---|---|---|---|---|---|---|---|---|---|---|---|---|
| $\vdots$ | $\vdots$ | $\vdots$ | $\vdots$ | $\vdots$ | $\vdots$ | $\vdots$ | $\vdots$ | $\vdots$ | $\vdots$ | $\vdots$ | $\vdots$ | $\vdots$ |
| $S_{1,6}$ | $S_{2,6}$ | $S_{3,6}$ | $S_{4,6}$ | $S_{5,6}$ | $S_{6,6}$ | $S_{7,6}$ | $S_{8,6}$ | $S_{9,6}$ | $S_{10,6}$ | $S_{11,6}$ | $\cdots$ | $S_{p,6}$ |
| $S_{1,5}$ | $S_{2,5}$ | $S_{3,5}$ | $S_{4,5}$ | $S_{5,5}$ | $S_{6,5}$ | $S_{7,5}$ | $S_{8,5}$ | $S_{9,5}$ | $S_{10,5}$ | $S_{11,5}$ | $\cdots$ | $S_{p,5}$ |
| $S_{1,4}$ | $S_{2,4}$ | $S_{3,4}$ | $S_{4,4}$ | $S_{5,4}$ | $S_{6,4}$ | $S_{7,4}$ | $S_{8,4}$ | $S_{9,4}$ | $S_{10,4}$ | $S_{11,4}$ | $\cdots$ | $S_{p,4}$ |
| $S_{1,3}$ | $S_{2,3}$ | $S_{3,3}$ | $S_{4,3}$ | $S_{5,3}$ | $S_{6,3}$ | $S_{7,3}$ | $S_{8,3}$ | $S_{9,3}$ | $S_{10,3}$ | $S_{11,3}$ | $\cdots$ | $S_{p,3}$ |
| $S_{1,2}$ | $S_{2,2}$ | $S_{3,2}$ | $S_{4,2}$ | $S_{5,2}$ | $S_{6,2}$ | $S_{7,2}$ | $S_{8,2}$ | $S_{9,2}$ | $S_{10,2}$ | $S_{11,2}$ | $\cdots$ | $S_{p,2}$ |
| $S_{1,1}$ | $S_{2,1}$ | $S_{3,1}$ | $S_{4,1}$ | $S_{5,1}$ | $S_{6,1}$ | $S_{7,1}$ | $S_{8,1}$ | $S_{9,1}$ | $S_{10,1}$ | $S_{11,1}$ | $\cdots$ | $S_{p,1}$ |
| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | $\cdots$ | $CH_p$ |

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | $\cdots$ | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | $\cdots$ | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | $\cdots$ | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | $\cdots$ | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | $\cdots$ | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | $\cdots$ | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | $\cdots$ | $P_{7,N}$ |
| $\vdots$ | $\vdots$ | $\vdots$ | $\vdots$ | $\vdots$ | $\vdots$ | $\vdots$ | $\vdots$ | $\vdots$ | $\vdots$ | $\vdots$ |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | $\cdots$ | $P_{M,N}$ |

|  |  |  |  |  |  |  |  |  |  |  |
|---|---|---|---|---|---|---|---|---|---|---|
|  |  |  |  |  |  |  |  |  |  |  |
| $S_{6,3}$ | $S_{6,3}$ |  |  |  |  |  |  |  |  | $S_{6,3}$ |
|  | $S_{6,3}$ | $S_{6,3}$ | $S_{6,3}$ | $S_{6,3}$ | $S_{6,3}$ | $S_{6,3}$ | $S_{6,3}$ | $S_{6,3}$ | ... |  |
|  |  |  |  |  |  |  |  |  |  |  |
|  |  |  |  |  |  |  |  |  |  |  |
|  |  |  |  |  |  |  |  |  |  |  |
|  |  |  |  |  |  |  |  |  |  |  |
|  |  |  |  |  |  |  |  |  |  |  |

| $S_{1,t}$ | $S_{2,t}$ | $S_{3,t}$ | $S_{4,t}$ | $S_{5,t}$ | $S_{6,t}$ | $S_{7,t}$ | $S_{8,t}$ | $S_{9,t}$ | $S_{10,t}$ | $S_{11,t}$ | ⋯ | $S_{p,t}$ |
|---|---|---|---|---|---|---|---|---|---|---|---|---|
| ⋮ | ⋮ | ⋮ | ⋮ | ⋮ | ⋮ | ⋮ | ⋮ | ⋮ | ⋮ | ⋮ | | ⋮ |
| $S_{1,6}$ | $S_{2,6}$ | $S_{3,6}$ | $S_{4,6}$ | $S_{5,6}$ | $S_{6,6}$ | $S_{7,6}$ | $S_{8,6}$ | $S_{9,6}$ | $S_{10,6}$ | $S_{11,6}$ | ⋯ | $S_{p,6}$ |
| $S_{1,5}$ | $S_{2,5}$ | $S_{3,5}$ | $S_{4,5}$ | $S_{5,5}$ | $S_{6,5}$ | $S_{7,5}$ | $S_{8,5}$ | $S_{9,5}$ | $S_{10,5}$ | $S_{11,5}$ | ⋯ | $S_{p,5}$ |
| $S_{1,4}$ | $S_{2,4}$ | $S_{3,4}$ | $S_{4,4}$ | $S_{5,4}$ | $S_{6,4}$ | $S_{7,4}$ | $S_{8,4}$ | $S_{9,4}$ | $S_{10,4}$ | $S_{11,4}$ | ⋯ | $S_{p,4}$ |
| $S_{1,3}$ | $S_{2,3}$ | $S_{3,3}$ | $S_{4,3}$ | $S_{5,3}$ | $S_{6,3}$ | $S_{7,3}$ | $S_{8,3}$ | $S_{9,3}$ | $S_{10,3}$ | $S_{11,3}$ | ⋯ | $S_{p,3}$ |
| $S_{1,2}$ | $S_{2,2}$ | $S_{3,2}$ | $S_{4,2}$ | $S_{5,2}$ | $S_{6,2}$ | $S_{7,2}$ | $S_{8,2}$ | $S_{9,2}$ | $S_{10,2}$ | $S_{11,2}$ | ⋯ | $S_{p,2}$ |
| $S_{1,1}$ | $S_{2,1}$ | $S_{3,1}$ | $S_{4,1}$ | $S_{5,1}$ | $S_{6,1}$ | $S_{7,1}$ | $S_{8,1}$ | $S_{9,1}$ | $S_{10,1}$ | $S_{11,1}$ | ⋯ | $S_{p,1}$ |
| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | ⋯ | $CH_p$ |

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | ⋯ | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | ⋯ | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | ⋯ | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | ⋯ | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | ⋯ | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | ⋯ | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | ⋯ | $P_{7,N}$ |
| ⋮ | ⋮ | ⋮ | ⋮ | ⋮ | ⋮ | ⋮ | ⋮ | ⋮ | | ⋮ |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | ⋯ | $P_{M,N}$ |

| | | | | | | | | | | |
|---|---|---|---|---|---|---|---|---|---|---|
| $S_{6,4}$ | | | | | | | | | | |
| $S_{6,3}$ $S_{6,4}$ | $S_{6,3}$ $S_{6,4}$ | | | | | | | | $S_{6,3}$ $S_{6,4}$ | |
| | $S_{6,3}$ $S_{6,4}$ | $S_{6,3}$ $S_{6,4}$ | $S_{6,3}$ $S_{6,4}$ | $S_{6,3}$ | $S_{6,3}$ | $S_{6,3}$ | $S_{6,3}$ | $S_{6,3}$ $S_{6,4}$ | ... | |
| | | | $S_{6,4}$ | $S_{6,4}$ | $S_{6,4}$ | $S_{6,4}$ | $S_{6,4}$ | $S_{6,4}$ | | |
| | | | | | | | | | | |
| | | | | | | | | | | |
| | | | | | | | | | | |
| | | | | | | | | | | |

PROVIDING MOTION MODE IMAGE IN ULTRASOUND SYSTEM

CROSS-REFERENCE TO RELATED APPLICATION

The present application claims priority from Korean Patent Application No. 10-2011-0143854 filed on Dec. 27, 2011, the entire subject matter of which is incorporated herein by reference.

TECHNICAL FIELD

The present disclosure generally relates to ultrasound systems, and more particularly to providing a motion mode image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of target objects (e.g., human organs).

The ultrasound system may provide ultrasound images of various modes including a brightness mode image representing reflection coefficients of ultrasound signals (i.e., ultrasound echo signals) reflected from a target object of a living body with a two-dimensional image, a Doppler mode image representing velocity of a moving target object with spectral Doppler by using a Doppler effect, a color Doppler mode image representing velocity of the moving target object with colors by using the Doppler effect, an elastic image representing mechanical characteristics of tissues before and after applying compression thereto, etc.

The ultrasound system may transmit ultrasound signals to the living body including a moving target object (e.g., blood flow) and receive ultrasound signals (i.e., ultrasound echo signals) from the living body. The ultrasound system may further form the color Doppler mode image representing velocities of the target object with colors based on the ultrasound echo signals. The color Doppler image may be used to diagnose disease of a blood vessel, a heart and the like. However, the color Doppler image may not represent an accurate motion of the target object since the respective colors in the color Doppler image indicate the velocity of the target object, which moves forward in a transmission direction of the ultrasound signals and backward in the transmission direction of the ultrasound signals.

To resolve this problem, vector Doppler methods capable of obtaining motion (i.e., velocity and direction) of the target object are used. A cross beam-based method of the vector Doppler methods acquires velocity components of the target object from at least two different directions, and combines the velocity components to form vector information including two-dimensional or three-dimensional direction information and velocity information.

SUMMARY

There are provided embodiments for providing a motion mode image corresponding to the motion of a target object.

In one embodiment, by way of non-limiting example, an ultrasound system comprises: a user input unit configured to receive input information for setting a region of interest on a brightness mode image; and a processing unit configured to form the brightness mode image based on first ultrasound data corresponding to a target object, and form vector information of the target object based on second ultrasound data corresponding to the target object, the processing unit being further configured to form a motion mode image including at least one of a brightness motion mode image and a color motion mode image based on the first ultrasound data and the vector information corresponding to the region of interest.

In another embodiment, there is provided a method of providing a motion mode image, comprising: a) forming a brightness mode image based on first ultrasound data corresponding to a target object; b) forming vector information of the target object based on second ultrasound data corresponding to the target object; c) receiving input information for setting a region of interest on the brightness mode image; and d) forming a motion mode image including at least one of a brightness motion mode image and a color motion mode image based on the first ultrasound data and the vector information corresponding to the region of interest.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIGS. 4 to 7 are schematic diagrams showing examples of transmission directions and reception directions.

FIG. 8 is a schematic diagram showing an example of sampling data and pixels of an ultrasound image.

FIGS. 9 to 12 are schematic diagrams showing examples of performing a receiving beam-forming.

FIG. 14 is a schematic diagram showing an example of setting a sampling data set.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
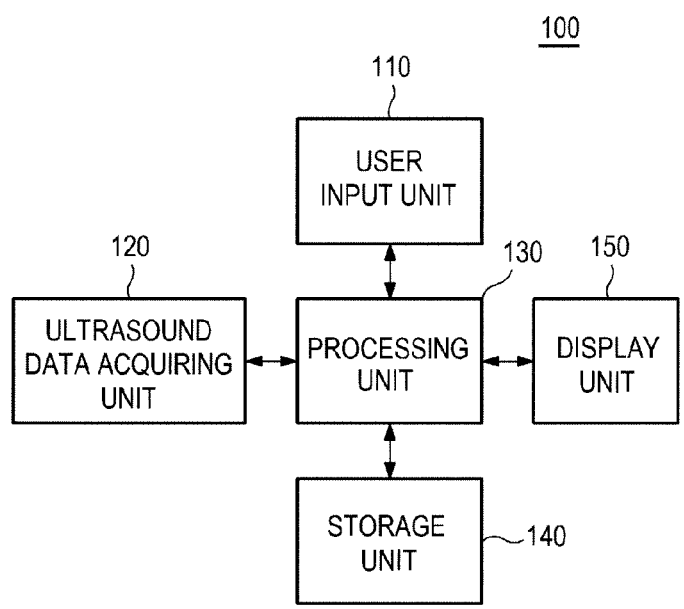
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110.

Figure 2:
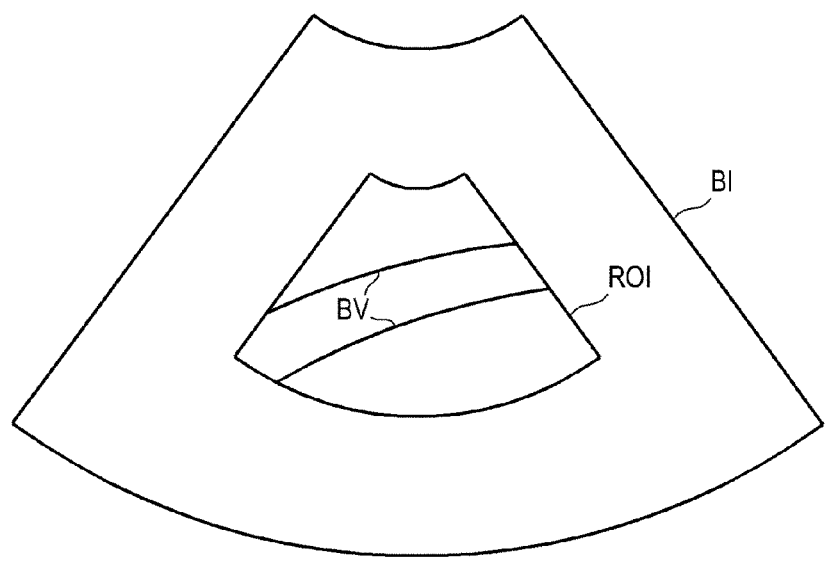
FIG. 2 is a schematic diagram showing an example of a brightness mode image and a region of interest.
Figure 17:
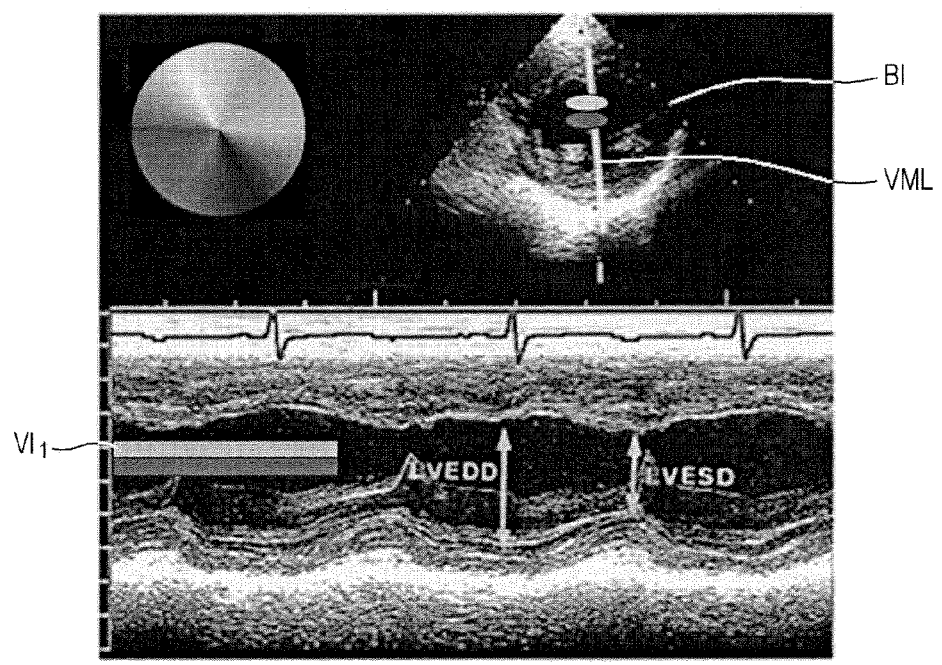
FIGS. 17 and 18 are schematic diagrams showing examples of motion mode images.
Figure 18:
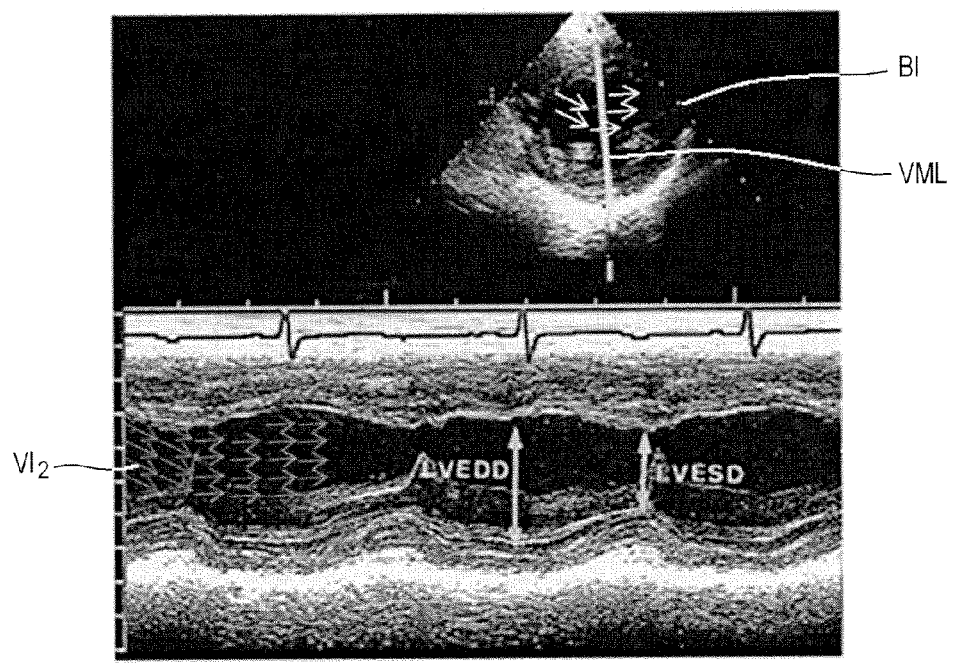

The user input unit 110 may be configured to receive input information from a user. In one embodiment, the input information may include first input information for setting a first region of interest ROI on a brightness mode image BI, as shown in FIG. 2. The first region of interest ROI may include a color box for obtaining vector information corresponding to motion (i.e., velocity and direction) of a target object. The input information may further include second input information for setting a second region of interest VML on the brightness mode image BI, as shown in FIGS. 17 and 18. The second region of interest VML may be a region of interest for obtaining a motion mode image. The second region of interest VML may be a straight line or a curve. However, it should be noted herein that the second region of interest VML may not be limited thereto. The motion mode image may be an image for representing how biological information of the target object varies with time based on at least one of vector information and ultrasound data of the target object. In FIG. 2, a reference numeral BV represents a blood vessel. The user input unit 110 may include a control panel, a track ball, a mouse, a keyboard and the like.

The ultrasound system 100 may further include an ultrasound data acquiring unit 120. The ultrasound data acquiring unit 120 may be configured to transmit ultrasound signals to a living body. The living body may include moving target objects (e.g., blood vessel, heart, blood flow, etc.). The ultrasound data acquiring unit 120 may be further configured to receive ultrasound signals (i.e., ultrasound echo signals) from the living body to acquire ultrasound data corresponding to an ultrasound image.

Figure 3:
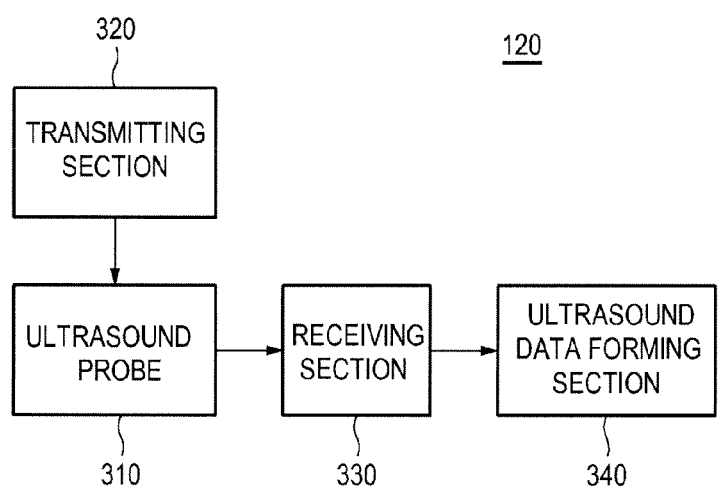
FIG. 3 is a block diagram showing an illustrative embodiment of an ultrasound data acquiring unit.

FIG. 3 is a block diagram showing an illustrative embodiment of the ultrasound data acquiring unit. Referring to FIG. 3, the ultrasound data acquiring unit 120 may include an ultrasound probe 310.

The ultrasound probe 310 may include a plurality of elements 311 (see FIG. 4) for reciprocally converting between ultrasound signals and electrical signals. The ultrasound probe 310 may be configured to transmit the ultrasound signals to the living body. The ultrasound signals transmitted from the ultrasound probe 310 may be plane wave signals that the ultrasound signals are not focused at a focusing point or focused signals that the ultrasound signals are focused at the focusing point. However, it should be noted herein that the ultrasound signals may not be limited thereto. The ultrasound probe 310 may be further configured to receive the ultrasound echo signals from the living body to output electrical signals (hereinafter, referred to as "reception signals"). The reception signals may be analog signals. The ultrasound probe 310 may include a convex probe, a linear probe and the like.

The ultrasound data acquiring unit 120 may further include a transmitting section 320. The transmitting section 320 may be configured to control the transmission of the ultrasound signals. The transmitting section 320 may be further configured to generate electrical signals (hereinafter, referred to as "transmission signals") in consideration of the elements 311.

In one embodiment, the transmitting section 320 may be configured to generate transmission signals (hereinafter, referred to as "brightness mode transmission signals") for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output reception signals (hereinafter, referred to as "brightness mode reception signals").

The transmitting section 320 may be further configured to generate transmission signals (hereinafter, referred to as "Doppler mode transmission signals") corresponding to an ensemble number in consideration of the elements 311 and at least one transmission direction of the ultrasound signals (i.e., transmission beam). Thus, the ultrasound probe 310 may be configured to convert the Doppler mode transmission signals provided from the transmitting section 320 into the ultrasound signals, transmit the ultrasound signals to the living body in the at least one transmission direction, and receive the ultrasound echo signals from the living body to output reception signals (hereinafter, referred to as "Doppler mode reception signals"). The ensemble number may represent the number of transmitting and receiving the ultrasound signals to/from a target object.

As one example, the transmitting section 320 may be configured to generate the Doppler mode transmission signals corresponding to the ensemble number in consideration of a transmission direction Tx and the elements 311, as shown in FIG. 4. The transmission direction may be one direction in the range of a direction (0 degree) perpendicular to a longitudinal direction of the elements 311 to a maximum steering direction of the transmission beam.

As another example, the transmitting section 320 may be configured to generate first Doppler mode transmission signals corresponding to the ensemble number in consideration of a first transmission direction $Tx_1$ and the elements 311, as shown in FIG. 5. Thus, the ultrasound probe 310 may be configured to convert the first Doppler mode transmission signals provided from the transmitting section 320 into the ultrasound signals, transmit the ultrasound signals to the living body in the first transmission direction $Tx_1$, and receive the ultrasound echo signals from the living body to output first Doppler mode reception signals. The transmitting section 320 may be further configured to generate second Doppler mode transmission signals corresponding to the ensemble number in consideration of a second transmission direction $Tx_2$ and the elements 311, as shown in FIG. 5. Thus, the ultrasound probe 310 may be configured to convert the second Doppler mode transmission signals provided from the transmitting section 320 into the ultrasound signals, transmit the ultrasound signals to the living body in the second transmission direction $Tx_2$, and receive the ultrasound echo signals from the living body to output second Doppler mode reception signals. In FIG. 5, a reference numeral PRI represents a pulse repeat interval.

In another embodiment, the transmitting section 320 may be configured to generate the brightness mode transmission signals for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output the brightness mode reception signals.

The transmitting section 320 may be further configured to generate the Doppler mode transmission signals corresponding to the ensemble number in consideration of the at least one transmission direction and the elements 311. Thus, the ultrasound probe 310 may be configured to convert the Doppler mode transmission signals provided from the transmitting section 320 into the ultrasound signals, transmit the ultrasound signals to the living body, and receive the ultrasound echo signals from the living body to output the Doppler mode reception signals. The ultrasound signals may be transmitted in an interleaved transmission scheme. The interleaved transmission scheme will be described below in detail.

For example, the transmitting section 320 may be configured to generate the first Doppler mode transmission signals in consideration of the first transmission direction $Tx_1$ and the elements 311, as shown in FIG. 6. Thus, the ultrasound probe 310 may be configured to convert the first Doppler mode transmission signals provided from the transmitting section 320 into the ultrasound signals, and transmit the ultrasound signals to the living body in the first transmission direction $Tx_1$. Thereafter, the transmitting section 320 may be further configured to generate the second Doppler mode transmission signals in consideration of the second transmission direction $Tx_2$ and the elements 311, as shown in FIG. 6. Thus, the ultrasound probe 310 may be configured to convert the second Doppler mode transmission signals provided from the transmitting section 320 into the ultrasound signals, and transmit the ultrasound signals to the living body in the second transmission direction $Tx_2$. The ultrasound probe 310 may be further configured to receive the ultrasound echo signals (i.e., ultrasound echo signals corresponding to first Doppler mode transmission signals) from the living body to output the first Doppler mode reception signals. The ultrasound probe 310 may be also configured to receive the ultrasound echo signals (i.e., ultrasound echo signals corresponding to second Doppler mode transmission signals) from the living body to output the second Doppler mode reception signals.

Thereafter, the transmitting section 320 may be configured to generate the first Doppler mode transmission signals based on the pulse repeat interval, as shown in FIG. 6. Thus, the ultrasound probe 310 may be configured to convert the first Doppler mode transmission signals provided from the transmitting section 320 into the ultrasound signals, and transmit the ultrasound signals to the living body in the first transmission direction $Tx_1$. The transmitting section 320 may be further configured to generate the second Doppler mode transmission signals based on the pulse repeat interval, as shown in FIG. 6. Thus, the ultrasound probe 310 may be configured to convert the second Doppler mode transmission signals provided from the transmitting section 320 into the ultrasound signals, and transmit the ultrasound signals to the living body in the second transmission direction $Tx_2$. The ultrasound probe 310 may be further configured to receive the ultrasound echo signals (i.e., ultrasound echo signals corresponding to first Doppler mode transmission signals) from the living body to output the first Doppler mode reception signals. The ultrasound probe 310 may be also configured to receive the ultrasound echo signals (i.e., ultrasound echo signals corresponding to second Doppler mode reception signals) from the living body to output the second Doppler mode reception signals.

As described above, the transmitting section 320 may be configured to generate the first Doppler mode transmission signals and the second Doppler mode transmission signals corresponding to the ensemble number.

In yet another embodiment, the transmitting section 320 may be configured to generate the brightness mode transmission signals for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output the brightness mode reception signals.

The transmitting section 320 may be further configured to generate the Doppler mode transmission signals corresponding to the ensemble number in consideration of the at least one transmission direction and the elements 311. Thus, the ultrasound probe 310 may be configured to convert the Doppler mode transmission signals provided from the transmitting section 320 into the ultrasound signals, transmit the ultrasound signals to the living body, and receive the ultrasound echo signals from the living body to output the Doppler mode reception signals. The ultrasound signals may be transmitted according to the pulse repeat interval.

For example, the transmitting section 320 may be configured to generate the first Doppler mode transmission signals in consideration of the first transmission direction $Tx_1$ and the elements 311 based on the pulse repeat interval, as shown in FIG. 7. As such, the ultrasound probe 310 may be configured to convert the first Doppler mode transmission signals provided from the transmitting section 320 into the ultrasound signals, transmit the ultrasound signals to living body in the first transmission direction $Tx_1$, and receive the ultrasound echo signals from the living body to output the first Doppler mode reception signals. The transmitting section 320 may be further configured to generate the second Doppler mode transmission signals in consideration of the second transmission direction $Tx_2$ and the elements 311 based on the pulse repeat interval, as shown in FIG. 7. Thus, the ultrasound probe 310 may be configured to convert the second Doppler mode transmission signals provided from the transmitting section 320 into the ultrasound signals, transmit the ultrasound signals to the living body in the second transmission direction $Tx_2$, and receive the ultrasound echo signals from the living body to output the second Doppler mode reception signals.

As described above, the transmitting section 320 may be configured to generate the first Doppler mode transmission signals and the second Doppler mode transmission signals corresponding to the ensemble number based on the pulse repeat interval.

Referring back to FIG. 3, the ultrasound data acquiring unit 120 may further include a receiving section 330. The receiving section 330 may be configured to perform an analog-digital conversion upon the reception signals provided from the ultrasound probe 310 to form sampling data of the reception signals. The receiving section 330 may be further configured to perform a reception beam-forming upon the sampling data in consideration of the elements 311 to form reception-focused data. The reception beam-forming will be described below in detail.

In one embodiment, the receiving section 330 may be configured to perform the analog-digital conversion upon the brightness mode reception signals provided from the ultrasound probe 310 to form sampling data (hereinafter, referred to as "brightness mode sampling data"). The receiving section 330 may be further configured to perform the reception beam-forming upon the brightness mode sampling data to form reception-focused data (hereinafter, referred to as "brightness mode reception-focused data").

The receiving section 330 may be further configured to perform the analog-digital conversion upon the Doppler mode reception signals provided from the ultrasound probe 310 to form sampling data (hereinafter, referred to as "Doppler mode sampling data"). The receiving section 330 may be further configured to perform the reception beam-forming upon the Doppler mode sampling data to form reception-focused data (hereinafter, referred to as "Doppler mode reception-focused data") corresponding to the at least one reception direction of the ultrasound echo signals (i.e., reception beam).

As one example, the receiving section 330 may be configured to perform the analog-digital conversion upon the Doppler mode reception signals provided from the ultrasound probe 310 to form the Doppler mode sampling data. The receiving section 330 may be further configured to perform the reception beam-forming upon the Doppler mode sampling data to form first Doppler mode reception-focused data corresponding to the first reception direction $Rx_1$ and second Doppler mode reception-focused data corresponding to the second reception direction $Rx_2$, as shown in FIG. 4.

As another example, the receiving section 330 may be configured to perform the analog-digital conversion upon the first Doppler mode reception signals provided from the ultrasound probe 310 to form first Doppler mode sampling data corresponding to the first transmission direction $Tx_1$, as shown in FIG. 5. The receiving section 330 may be further configured to perform the reception beam-forming upon the first Doppler mode sampling data to form the first Doppler mode reception-focused data corresponding to the first reception direction $Rx_1$. The receiving section 330 may be also configured to perform the analog-digital conversion upon the second Doppler mode reception signals provided from the ultrasound probe 310 to form second Doppler mode sampling data corresponding to the second transmission direction $Tx_2$, as shown in FIG. 5. The receiving section 330 may be further configured to perform the reception beam-forming upon the second Doppler mode sampling data to form the second Doppler mode reception-focused data corresponding to the second reception direction $Rx_2$. If the reception direction is perpendicular to the elements 311 of the ultrasound probe 310, then an aperture size of being capable of receiving the ultrasound signals can be a maximum value.

The reception beam-forming may be described with reference to the accompanying drawings.

In one embodiment, the receiving section 330 may be configured to perform the analog-digital conversion upon the reception signals provided through a plurality of channels $CH_k$, wherein $1 \leq k \leq N$, from the ultrasound probe 310 to form sampling data $S_{i,j}$, wherein the i and j are a positive integer, as shown in FIG. 8. The sampling data $S_{i,j}$ may be stored in a storage unit 140. The receiving section 330 may be further configured to detect pixels corresponding to the sampling data based on positions of the elements 311 and orientation of pixels $P_{a,b}$, wherein $1 \leq a \leq M$, $1 \leq b \leq N$, of the ultrasound image UI with respect to the elements 311. That is, the receiving section 330 may select the pixels that the respective sampling data are used as pixel data thereof, during the reception beam-forming based on the positions of the elements 311 and the orientation of the respective pixels of the ultrasound image UI with respect to the elements 311. The receiving section 330 may be further configured to cumulatively assign the sampling data corresponding to the selected pixels as the pixel data.

Figure 10:
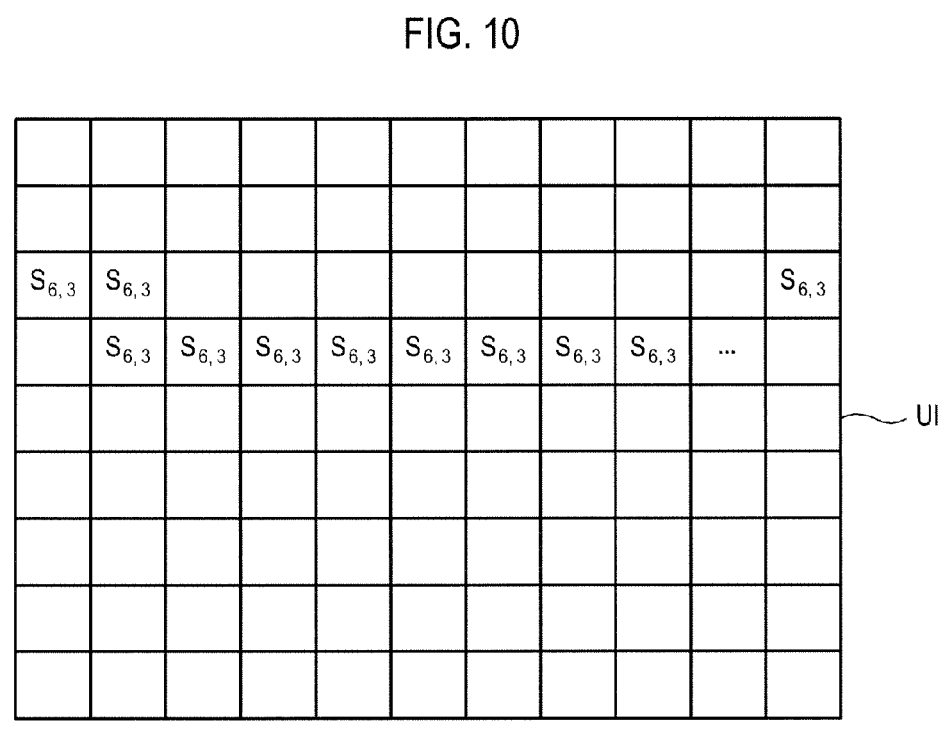

For example, the receiving section 330 may be configured to set a curve (hereinafter, referred to as "reception beam-forming curve") $CV_{6,3}$ for selecting pixels that the sampling data $S_{6,3}$ are used as the pixel data thereof, during the reception beam-forming based on the positions of the elements 311 and the orientation of the respective pixels of the ultrasound image UI with respect to the elements 311, as shown in FIG. 9. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ corresponding to the reception beam-forming curve $CV_{6,3}$ from the pixels $P_{a,b}$ of the ultrasound image UI, wherein $1 \leq a \leq M$, $1 \leq b \leq N$. That is, the receiving section 330 may select the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ on which the reception beam-forming curve $CV_{6,3}$ passes among the pixels $P_{a,b}$ of the ultrasound image UI. The receiving section 330 may be further configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, $P_{3,N}$, as shown in FIG. 10.

Thereafter, the receiving section 330 may be configured to set a reception beam-forming curve $CV_{6,4}$ for selecting pixels that the sampling data $S_{6,4}$ are used as the pixel data thereof during the reception beam-forming based on the positions of the elements 311 and the orientation of the respective pixels of the ultrasound image UI with respect to the elements 311, as shown in FIG. 11. The receiving section 330 may be further configured to detect the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, ... $P_{4,N}$, $P_{3,N}$ corresponding to the reception beam-forming curve $CV_{6,4}$ from the pixels $P_{a,b}$ of the ultrasound image UI. That is, the receiving section 330 may select the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, ... $P_{4,N}$, $P_{3,N}$ on which the reception beam-forming curve $CV_{6,4}$ passes among the pixels $P_{a,b}$ of the ultrasound image UI. The receiving section 330 may be also configured to assign the sampling data $S_{6,4}$ to the selected pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, ... $P_{4,N}$, $P_{3,N}$, as shown in FIG. 12. In this way, the respective sampling data, which are used as the pixel data, may be cumulatively assigned to the pixels as the pixel data.

The receiving section 330 may be configured to perform the reception beam-forming (i.e., summing) upon the sampling data which are cumulatively assigned to the respective pixels $P_{a,b}$ of the ultrasound image UI to form the reception-focused data.

In another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 8. The sampling data $S_{i,j}$ may be stored in the storage unit 140. The receiving section 330 may be further configured to detect pixels corresponding to the sampling data based on the positions of the elements 311 and the orientation of the pixels of the ultrasound image UI with respect to the elements 311. That is, the receiving section 330 may select the pixels that the respective sampling data are used as the pixel data thereof during the reception beam-forming based on the positions of the elements 311 and the orientation of the respective pixels of the ultrasound image UI with respect to the elements 311. The receiving section 330 may be configured to cumulatively assign the sampling data corresponding to the selected pixels as the pixel data. The receiving section 330 may be further configured to determine pixels existing in the same column among the selected pixels. The receiving section 330 may be also configured to set weights corresponding to the respective determined pixels. The receiving section 330 may be further configured to apply the weights to the sampling data of the respective pixels.

Figure 13:
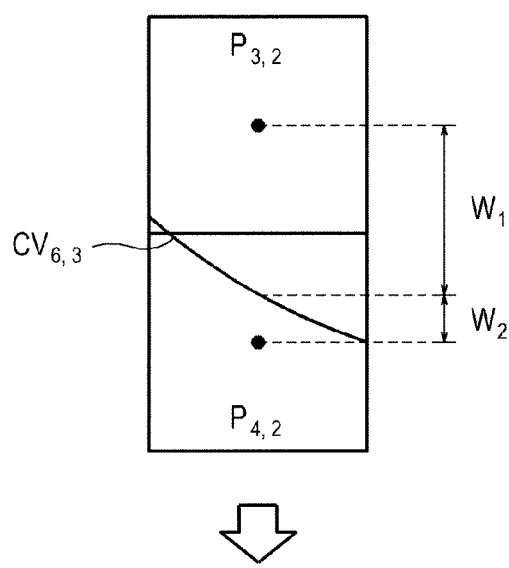
FIG. 13 is a schematic diagram showing an example of setting weights.

For example, the receiving section 330 may be configured to set the reception beam-forming curve $CV_{6,3}$ for selecting pixels that the sampling data $S_{6,3}$ are used as the pixel data thereof during the reception beam-forming based on the positions of the elements 311 and the orientation of the respective pixels of the ultrasound image UI with respect to the elements 311, as shown in FIG. 9. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ corresponding to the reception beam-forming curve $CV_{6,3}$ from the pixels $P_{a,b}$ of the ultrasound image UI. That is, the receiving section 330 may select the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ on which the reception beam-forming curve $CV_{6,3}$ passes among the pixels $P_{a,b}$ of the ultrasound image UI. The receiving section 330 may be further configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$, as shown in FIG. 10. The receiving section 330 may be further configured to determine pixels $P_{3,2}$ and $P_{4,2}$ which exist in the same column among the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, $P_{3,N}$. The receiving section 330 may be further configured to calculate a distance $W_1$ from a center of the determined pixel $P_{3,2}$ to the reception beam-forming curve $CV_{6,3}$ and a distance $W_2$ from a center of the determined pixel $P_{4,2}$ to the reception beam-forming curve $CV_{6,3}$, as shown in FIG. 13. The receiving section 330 may be also configured to set a first weight $\alpha_1$ corresponding to the pixel $P_{3,2}$ based on the distance $W_1$ and a second weight $\alpha_2$ corresponding to the pixel $P_{4,2}$ based on the distance $W_2$. The first weight $\alpha_1$ and the second weight $\alpha_2$ may be set to be in proportion to or in inverse proportion to the calculated distances. The receiving section 330 may be further configured to apply the first weight $\alpha_1$ to the sampling data $S_{6,3}$ assigned to the pixel $P_{3,2}$ and to apply the second weight $\alpha_2$ to the sampling data $S_{6,3}$ assigned to the pixel $P_{4,2}$. The receiving section 330 may be configured to perform the above process upon the remaining sampling data.

The receiving section 330 may be configured to perform the reception beam-forming upon the sampling data which are cumulatively assigned to the respective pixels $P_{a,b}$ of the ultrasound image UI to form the reception-focused data.

In yet another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 8. The sampling data $S_{i,j}$ may be stored in the storage unit 140. The receiving section 330 may be further configured to set a sampling data set for selecting pixels that the sampling data $S_{i,j}$ are used as the pixel data thereof during the reception beam-forming.

Figure 14:
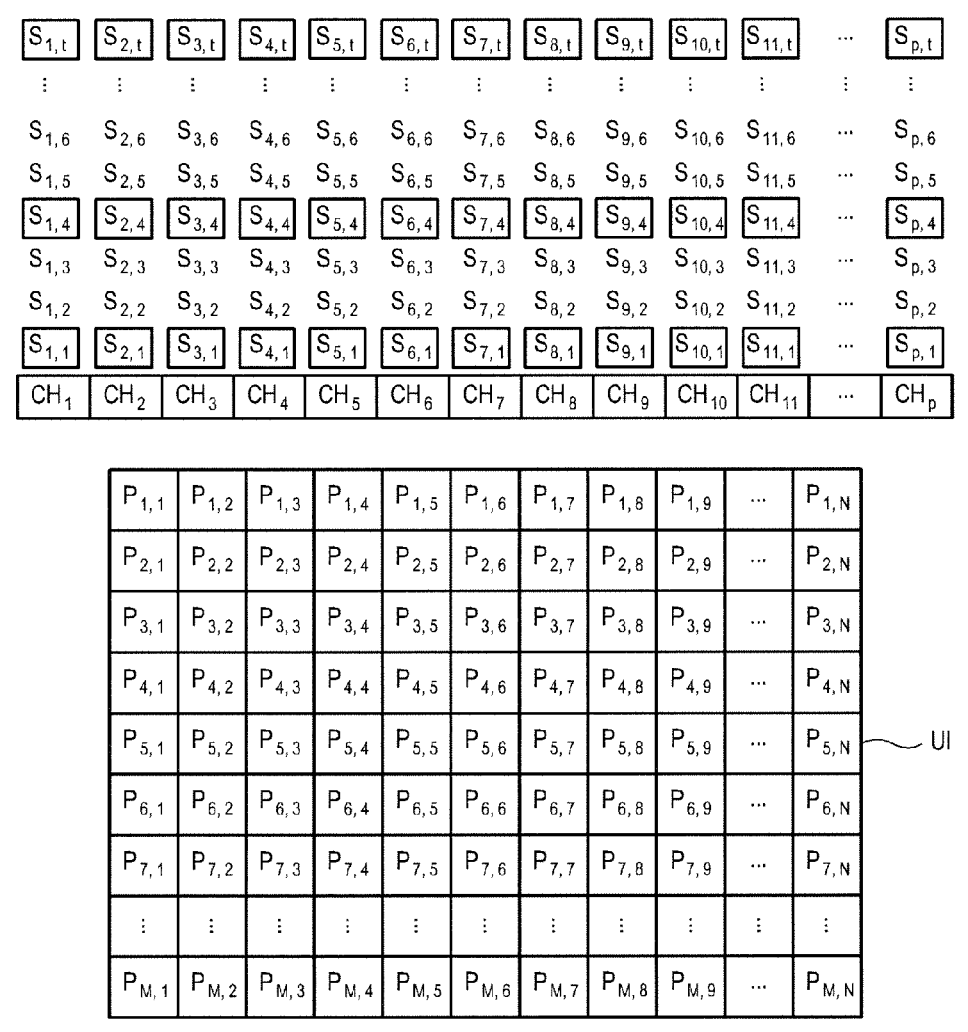

For example, the receiving section 330 may be configured to set the sampling data $S_{1,1}$, $S_{1,4}$, ... $S_{1,t}$, $S_{2,1}$, $S_{2,4}$, ... $S_{2,t}$, ... $S_{p,t}$, as the sampling data set (denoted by a box) for selecting the pixels that the sampling data $S_{i,j}$ are used as the pixel data thereof during the reception beam-forming, as shown in FIG. 14.

The receiving section 330 may be further configured to detect the pixels corresponding to the respective sampling data of the sampling data set based on the positions of the elements 311 and the orientation of the respective pixels of the ultrasound image UI with respect to the elements 311. That is, the receiving section 330 may select the pixels that the respective sampling data of the sampling data set are used as the pixel data thereof during the reception beam-forming based on the positions of the elements 311 and the orientation of the respective pixels of the ultrasound image UI with respect to the elements 311. The receiving section 330 may be further configured to cumulatively assign the sampling data to the selected pixels in the same manner as the above embodiments. The receiving section 330 may be further configured to perform the reception beam-forming upon the sampling data, which are cumulatively assigned to the respective pixels of the ultrasound image UI to form the reception-focused data.

In yet another embodiment, the receiving section 330 may be configured to perform a down-sampling upon the reception signals provided through the plurality of channels $CH_k$ from the ultrasound probe 310 to form down-sampling data. As described above, the receiving section 330 may be further configured to detect the pixels corresponding to the respective sampling data based on the positions of the elements 311 and the orientation of the respective pixels of the ultrasound image UI with respect to the elements 311. That is, the receiving section 330 may select the pixels that the respective sampling data are used as the pixel data thereof during the reception beam-forming based on the positions of the elements 311 and the orientation of the pixels of the ultrasound image UI with respect to the elements 311. The receiving section 330 may be further configured to cumulatively assign the respective sampling data to the selected pixels in the same manner as the above embodiments. The receiving section 330 may be further configured to perform the reception beam-forming upon the sampling data, which are cumulatively assigned to the respective pixels of the ultrasound image UI to form the reception-focused data.

However, it should be noted herein that the reception beam-forming may not be limited thereto.

Referring back to FIG. 3, the ultrasound data acquiring unit 120 may further include an ultrasound data forming section 340. The ultrasound data forming section 340 may be configured to form the ultrasound data corresponding to the ultrasound image based on the reception-focused data provided from the receiving section 330. The ultrasound data forming section 340 may be further configured to perform a signal process (e.g., gain control, etc.) upon the reception-focused data.

In one embodiment, the ultrasound data forming section 340 may be configured to form ultrasound data (hereinafter, referred to as "brightness mode ultrasound data") corresponding to the brightness mode image based on the brightness mode reception-focused data provided from the receiving section 330. The brightness mode ultrasound data may include radio frequency data.

The ultrasound data forming section 340 may be further configured to form ultrasound data (hereinafter, referred to as "Doppler mode ultrasound data") corresponding to the region of interest ROI based on the Doppler mode reception-focused data provided from the receiving section 330. The Doppler mode ultrasound data may include in-phase/quadrature data. However, it should be noted herein that the Doppler mode ultrasound data may not be limited thereto.

For example, the ultrasound data forming section 340 may form first Doppler mode ultrasound data based on the first Doppler mode reception-focused data provided from the receiving section 330. The ultrasound data forming section 340 may further form second Doppler mode ultrasound data based on the second Doppler mode reception-focused data provided from the receiving section 330.

Referring back to FIG. 1, the ultrasound system 100 may further include a processing unit 130 in communication with the user input unit 110 and the ultrasound data acquiring unit 120. The processing unit 130 may include a central processing unit, a microprocessor, a graphic processing unit and the like.

Figure 15:
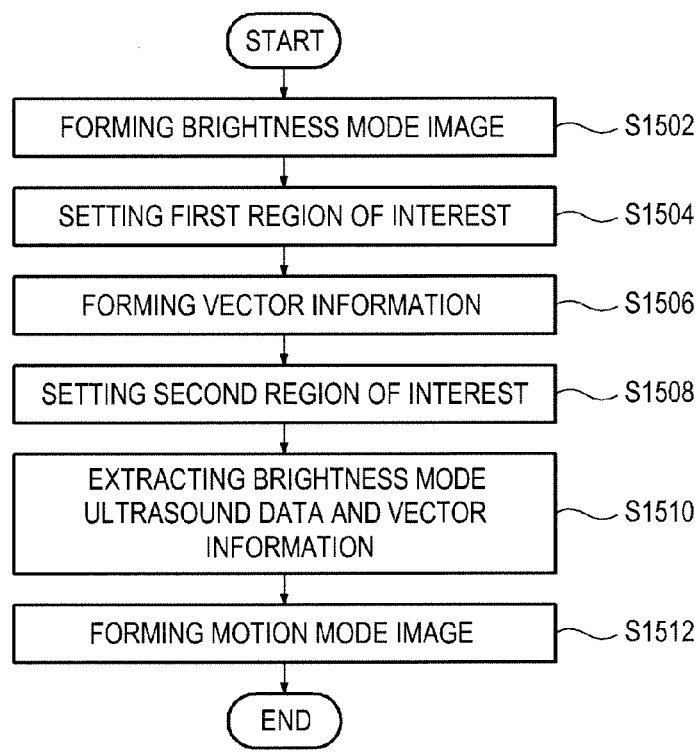
FIG. 15 is a flow chart showing a process of forming a motion mode image.

FIG. 15 is a flow chart showing a process of forming the motion mode image. The processing unit 130 may be configured to form the brightness mode image BI based on the brightness mode ultrasound data provided from the ultrasound data acquiring unit 120, at step S1502 in FIG. 15. The brightness mode image BI may be displayed on a display unit 150.

The processing unit 130 may be configured to set the first region of interest ROI on the brightness mode image BI based on the input information (i.e., first input information) provided from the user input unit 110, at step S1504 in FIG. 15. Thus, the ultrasound data acquiring unit 120 may be configured to transmit the ultrasound signals to the living body and receive the ultrasound echo signals from the living body to acquire the Doppler mode ultrasound data in consideration of the first region of interest ROI.

The processing unit 130 may be configured to form the vector information based on the Doppler mode ultrasound data provided from the ultrasound data acquiring unit 120, at step S1506 in FIG. 15. That is, the processing unit 130 may form the vector information corresponding to motion (i.e., velocity and direction) of the target object based on the Doppler mode ultrasound data.

Generally, when the transmission direction of the ultrasound signals is equal to the reception direction of the ultrasound echo signals and a Doppler angle is θ, the following relationship may be established:

$$X\cos\theta = \frac{C_0 f_d}{2 f_0} \quad (1)$$

In Equation 1, X represents a reflector velocity (i.e., velocity of a target object), $C_0$ represents a sound speed in the living body, $f_d$ represents a Doppler shift frequency, and $f_0$ represents an ultrasound frequency.

The Doppler shift frequency $f_d$ may be calculated by the difference between a frequency of the ultrasound signals (i.e., transmission beam) and a frequency of the ultrasound echo signals (i.e., reception beam). Also, the velocity component X cos θ projected to the transmission direction may be calculated by Equation 1.

When the transmission direction of the ultrasound signals (i.e., transmission beam) is different from the reception direction of the ultrasound echo signals (i.e., reception beam), the following relationship may be established:

$$X\cos\theta_T + X\cos\theta_R = \frac{C_0 f_d}{f_0} \quad (2)$$

In Equation 2, $\theta_T$ represents an angle between the ultrasound signals (i.e., transmission beam) and the blood flow, and $\theta_R$ represents an angle between the ultrasound echo signals (i.e., reception beam) and the blood flow.

Figure 16:
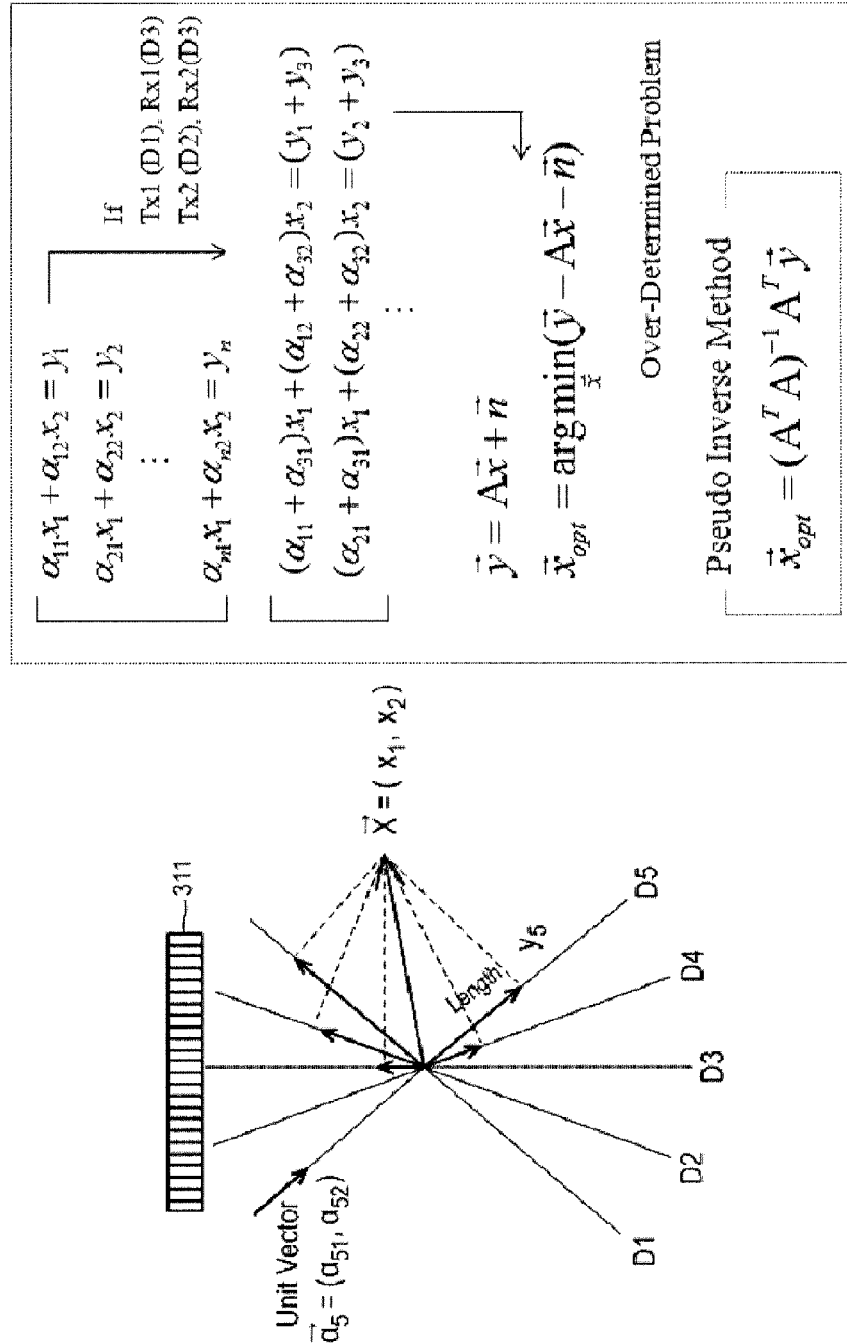
FIG. 16 is a schematic diagram showing an example of the transmission directions, the reception directions, the vector information and an over-determined problem.

FIG. 16 is a schematic diagram showing an example of the transmission directions, the reception directions, the vector information and an over-determined problem. Referring to FIG. 16, when the ultrasound signals (i.e., transmission beam) are transmitted in a first direction D1 and the ultrasound echo signals (i.e., reception beam) are received in the first direction D1, the following relationship may be established:

$$\vec{\alpha}_1 \vec{X} = \alpha_{11} x_1 + \alpha_{12} x_2 = y_1 = X\cos\theta \quad (3)$$

In Equation 3, $\vec{\alpha}_1 = (\alpha_{11}, \alpha_{12})$ represents a unit vector of the first direction D1, $\vec{X} = (x_1, x_2)$ represents variables, and $y_1$ is calculated by Equation 1.

When the ultrasound signals (i.e., transmission beam) are transmitted in a second direction D2 and the ultrasound echo signals (i.e., reception beam) are received in a third direction D3, the following relationship may be established:

$$(\alpha_{21} + \alpha_{31}) x_1 + (\alpha_{22} + \alpha_{32}) x_2 = (y_2 + y_3) = X\cos\theta_2 + X\cos\theta_3 \quad (4)$$

Equations 3 and 4 may be set to assume two-dimensional environment. Further, Equations 3 and 4 may be expanded to three-dimensional environment. That is, when expanding Equations 3 and 4 to the three-dimensional environment, the following relationship may be established:

$$\alpha_{11} x_1 + \alpha_{12} x_2 + \alpha_{13} x_3 = y \quad (5)$$

In the case of the two-dimensional environment (i.e., two-dimensional vector), at least two equations are required to calculate the variables $x_1$ and $x_2$. For example, when the ultrasound signals (i.e., transmission beam) are transmitted in the third direction D3 and the ultrasound echo signals (i.e., reception beam) are received in the second direction D2 and a fourth direction D4 as shown in FIG. 16, the following equations may be established:

$$(\alpha_{31} + \alpha_{21}) x_1 + (\alpha_{32} + \alpha_{22}) x_2 = (y_3 + y_2)$$

$$(\alpha_{31} + \alpha_{41}) x_1 + (\alpha_{32} + \alpha_{42}) x_2 = (y_3 + y_4) \quad (6)$$

The vector $\vec{X} = (x_1, x_2)$ may be calculated by the equations of Equation 6.

When the reception beam-forming is performed in at least two angles (i.e., at least two reception directions), at least two equations may be obtained and represented as the over-determined problem, as shown in FIG. 16. The over-determined problem may be solved by a pseudo inverse method, a weighted least square method and the like based on noise characteristics added to the Doppler shift frequency. The over-determined problem is well known in the art. Thus, it has not been described in detail so as not to unnecessarily obscure the present disclosure.

That is, M×N equations may be obtained by M transmission directions and the reception beam-forming of N reception directions at every transmission.

Referring back to FIG. 15, the processing unit 130 may be configured to set the second region of interest VML on the brightness mode image BI based on the input information (i.e., second input information) provided from the user input unit 110, at step S1508 in FIG. 15.

The processing unit 130 may be configured to extract brightness mode ultrasound data and vector information corresponding to the second region of interest VML from the brightness mode ultrasound data and the vector information, at step S1510 in FIG. 15. The processing unit 130 may be configured to form the motion mode image based on the extracted brightness mode ultrasound data and vector information, at step S1512 in FIG. 15.

As one example, the processing unit 130 may form a brightness motion mode image based on the extracted brightness mode ultrasound data, as shown in FIG. 17. The methods of forming the brightness motion mode image are well known in the art. Thus, they have not been described in detail so as not to unnecessarily obscure the present disclosure. The processing unit 130 may further form a color motion mode image $VI_1$ for representing the velocity and the direction of the target object as colors based on the extracted vector information, as shown in FIG. 17. The methods of forming the color motion mode image are well known in the art. Thus, they have not been described in detail so as not to unnecessarily obscure the present disclosure. The processing unit 130 may further form the motion mode image based on at least one of the brightness motion mode image and the color motion mode image. That is, the processing unit 130 may form the motion mode image including the at least one of the brightness motion mode image and the color motion mode image.

As another example, the processing unit 130 may form the brightness motion mode image based on the extracted brightness mode ultrasound data, as shown in FIG. 18. The processing unit 130 may further form the color motion mode image $VI_2$ for representing the velocity and the direction of the target object as color vectors based on the extracted vector information, as shown in FIG. 18. The processing unit 130 may further form the motion mode image based on at least one of the brightness motion mode image and the color motion mode image. That is, the processing unit 130 may form the motion mode image including the at least one of the brightness motion mode image and the color motion mode image.

Optionally, the processing unit 130 may be configured to form a Doppler mode image based on the vector information. The Doppler mode image may include a vector Doppler image or a color Doppler image. However, it should be noted herein that the Doppler mode image may not be limited thereto.

Referring back to FIG. 1, the ultrasound system 100 may further include the storage unit 140. The storage unit 140 may store the ultrasound data (i.e., brightness mode ultrasound data and Doppler mode ultrasound data) acquired by the ultrasound data acquiring unit 120. The storage unit 140 may further store the vector information formed by the processing unit 130.

The ultrasound system 100 may further include the display unit 150. The display unit 150 may be configured to display the brightness mode image formed by the processing unit 130. The display unit 150 may be further configured to display the motion mode image formed by the processing unit 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
a processor configured to form a brightness mode image based on first ultrasound data corresponding to a target object and to form vector information corresponding to a velocity and a moving direction of the target object based on second ultrasound data corresponding to the target object;
a display configured to display the brightness mode image; and
a user input, connected to the processor, configured to receive input information for setting a region of interest on the brightness mode image,
wherein the processor being further configured to form a brightness motion mode image of the region of interest based on the first ultrasound data corresponding to the region of interest and to form color vectors for representing the velocity and the moving direction of the target objects included in the region of interest based on the vector information corresponding to the region of interest,
wherein the display is configured to display the brightness motion mode image and to display the color vectors on the brightness motion mode image, and
wherein the color vectors include colors for representing the velocity of the target objects and arrows for representing the moving direction of the target objects.

2. The ultrasound system of claim 1, further comprising:
an ultrasound data acquiring unit having an ultrasound probe configured to transmit ultrasound signals to a living body including the target object in at least one transmission direction and receive ultrasound echo signals from the living body in at least one reception direction to acquire the second ultrasound data corresponding to the at least one reception direction.

3. The ultrasound system of claim 2, wherein the ultrasound data acquiring unit is configured to:
transmit the ultrasound signals to the living body in a first transmission direction; and
receive the ultrasound echo signals from the living body in a first reception direction and a second reception direction to acquire the second ultrasound data corresponding to the respective first and second reception directions.

4. The ultrasound system of claim 2, wherein the ultrasound data acquiring unit is configured to:
transmit the ultrasound signals to the living body in a first transmission direction and a second transmission direction; and
receive the ultrasound echo signals from the living body in a first reception direction to acquire the second ultrasound data corresponding to the first reception direction of the respective first and second transmission directions.

5. The ultrasound system of claim 2, wherein the ultrasound data acquiring unit is configured to:
transmit the ultrasound signals to the living body in a first transmission direction and a second transmission direction; and
receive the ultrasound echo signals from the living body in a first reception direction and a second reception direction to acquire the second ultrasound data corresponding to the respective first and second reception directions.

6. The ultrasound system of claim 2, wherein the ultrasound data acquiring unit is configured to transmit the ultrasound signals in an interleaved transmission scheme.

7. The ultrasound system of claim 2, wherein the ultrasound data acquiring unit transmits ultrasound signals which include plane wave signals or focused signals.

8. The ultrasound system of claim 1, wherein the user input receives input information for setting a region of interest which includes a straight line or a curved line.

9. The ultrasound system of claim 1, wherein the processor is configured to form the vector information corresponding to the velocity and the moving direction of the target object in consideration of at least one transmission direction and at least one reception direction corresponding to the at least one transmission direction.

10. The ultrasound system of claim 9, wherein the processor is configured to:
extract first ultrasound data and vector information corresponding to the region of interest from the first ultrasound data and the vector information.

* * * * *